(12) United States Patent
Chen

(10) Patent No.: US 6,303,700 B1
(45) Date of Patent: Oct. 16, 2001

(54) ADHESIVE AGENT AND USE OF SUCH ADHESIVE AGENT

(75) Inventor: Fei Chen, Lynge (DK)

(73) Assignee: Coloplast A/S, Hunlebaek (DK)

( * ) Notice: Subject to any disclaimer, the term of this patent is extended or adjusted under 35 U.S.C. 154(b) by 0 days.

(21) Appl. No.: 09/403,755

(22) PCT Filed: Apr. 29, 1998

(86) PCT No.: PCT/DK98/00166

§ 371 Date: Oct. 29, 1999

§ 102(e) Date: Oct. 29, 1999

(87) PCT Pub. No.: WO98/48858

PCT Pub. Date: Nov. 5, 1998

(30) Foreign Application Priority Data

Apr. 30, 1997 (DK) .................................................. 0489/97

(51) Int. Cl.[7] .................. C08F 126/10; C08F 226/10; C08L 15/00; A61L 15/24
(52) U.S. Cl. .................. 525/326.9; 523/111; 424/448
(58) Field of Search ................... 525/326.9; 523/111; 424/448

(56) References Cited

U.S. PATENT DOCUMENTS

| | | | |
|---|---|---|---|
| 3,339,549 | 9/1967 | Morse | 128/290 |
| 4,192,785 | 3/1980 | Chen et al. | 260/17.4 |
| 4,477,325 | 10/1984 | Osburn | 204/159.12 |
| 4,496,357 | 1/1985 | Osburn | 604/336 |
| 4,551,490 | 11/1985 | Doyle et al. | 524/22 |
| 5,133,821 | 7/1992 | Jensen | 156/245 |
| 5,176,916 * | 1/1993 | Yamanaka et al. | 424/448 |
| 5,320,838 | 6/1994 | Woller | 424/78.02 |

FOREIGN PATENT DOCUMENTS

| | | |
|---|---|---|
| 0 017 401 | 10/1980 | (EP) . |
| 0 063 898 | 11/1982 | (EP) . |
| 0 130 061 | 1/1985 | (EP) . |
| 0 122 344 | 7/1987 | (EP) . |
| 0 343 807 | 11/1989 | (EP) . |
| 0 264 299 | 1/1993 | (EP) . |
| 0 340 945 | 11/1993 | (EP) . |
| 0 591 898 | 4/1994 | (EP) . |
| 07265352A | 10/1995 | (JP) . |
| WO95/18603 | 7/1995 | (WO) . |

* cited by examiner

Primary Examiner—James J. Seidleck
Assistant Examiner—Olga Asinovsky
(74) Attorney, Agent, or Firm—Jacobson Holman, PLLC

(57) ABSTRACT

A pressure sensitive adhesive composition suitable for application to human or animal skin comprising a conjugated diene polymer, a polyvinyl pyrrolidone polymer or a polyvinyl pyrrolidine vinylacetate copolymer, optionally one or more hydrocolloids and optionally a physically cross-linked elastomer selected from block-copolymers comprising styrene and one or more butadienes improves the rate of absorption of water and improves the integrity of the adhesive composition as well as the tack of an adhesive agent on wet skin.

13 Claims, No Drawings

ADHESIVE AGENT AND USE OF SUCH ADHESIVE AGENT

BACKGROUND OF THE INVENTION

1. Field of the Invention

The invention relates to a pressure sensitive adhesive composition suitable for application to human or animal skin, to a method for preparing such adhesives and the use of such adhesive for the preparation of a wound dressing or an adhesive wafer for an ostomy appliance or the use of the adhesive agent for securing of and sealing around ostomy bandages, for securing wound dressings, for securing of devices for collecting urine, wound-drainage bandages, orthoses and prostheses and for protecting skin areas and parts of the body against pressure, impacts and friction. Furthermore, the invention relates to ostomy appliances and wound dressings comprising such adhesive composition.

2. Description of the Related Art

Various skin adhesive agents are used today for the above mentioned purposes.

A very widespread embodiment of skin adhesive agents comprises a self-adhesive elastomeric matrix, in which water-absorbing, swelling particles, the so-called hydrocolloids, are dispersed.

Adhesive compositions comprising hydrocolloids have been known for many years. U.S. Pat. No. 3,339,549 discloses a blend of a rubbery elastomer such as polyisobutylene and one or more water soluble or water swellable hydrocolloids such as a powdery mixture of pectin, gelatine and carboxymethylcellulose. The adhesive mass has a water-insoluble film applied to one surface. A composition of this type is available commercially from E. R. Squibb & Sons Inc. under the trademark "Stomahesive" and is used as a skin barrier around stomas to prevent skin breakdown by the corrosive fluids discharged by the stoma.

In adhesive compositions of this type, the polyisobutylene is responsible for provision of the adhesive properties and the dispersed hydrocolloid powders absorb fluid and render the adhesive agent capable of also adhering to moist skin (wet tack). These compositions are also gaining increasing acceptance as wound dressings for dermal ulcers, burns and other exuding wounds.

One major problem which has been encountered with conventional adhesive compositions comprising hydrocolloids is their susceptibility to breakdown upon exposure to body fluids. When the compositions are used as skin barriers, e.g., around stomas, absorption of fluid is desirable, but excessive swelling causes the composition to lose its integrity opening for leaks and the barrier must be replaced more often than is desirable from a skin protection point of view, and very often, a residue remains on the skin, which in many cases is difficulty to remove.

Another major problem for conventional adhesive compositions comprising hydrocolloids is their limited capability in adhering to moist body surfaces. There is particularly a need for an improved adhesive composition having an enhanced adhesion to moist skin in the management of ostomy patients, as it is often difficult to keep the skin around stomas completely dry during replacement of an ostomy appliance.

When bandaging wounds, contact with the wound exudate will in a similar way effect a disintegration of the adhesive agent which means that when the bandage is changed remnants will be left in the wound, which remnants may affect the wound-healing process. Besides during use, leakage may arise which partly means reduced time of use, and partly may increase the risk of contaminating the wound with bacteria or other microorganisms.

Adhesive agents are also used for securing devices, such as uridomas, for collecting the urine from incontinent men. Disintegration of the adhesive agent due to contact with urine will again mean a risk of leakage and a reduction of the time of use.

Adhesive agents are also employed for securing orthoses and prostheses (e.g., breast prostheses) and for protection of skin areas or parts of the body against pressure, impact and friction. In these cases it is primarily the secretion of sweat which may cause swelling and disintegration of the adhesive agent. When removing the adhesive agent remnants will be left on the skin, involving the inconveniences earlier mentioned.

A number of attempts have been made to improve the integrity of adhesive compositions.

As a method for improving the adhesive integrity, the use of hydrocolloids has been described which, in themselves, are cross-linked (e.g., cross-linked carboxymethylcellulose (CMC), cross-linked dextrane and other water-absorbing, but insoluble hydrocolloids). They will not dissolve due to the cross-linked structure. During the swelling process the individual particles will, therefore, obtain a gel-like structure, but no coherent gel could be formed since the macromolecules of the cross-linked hydrocolloids are locked in the gel network constituted by the individual particles. Due to the lack of a coherent gel, the cross-linked hydrocolloids will be leached out and suspended in the body fluids and the effect on the integrity of the swelled adhesive, therefore, is limited.

Alternatively, as described below, it has been tried to increase the integrity of the swelled adhesive agent by increasing the cohesion of the elastomeric phase. The elastomeric phase, therefore, will not so easily be split by the expanding hydrocolloids during the swelling process. This process, however, has a number of drawbacks:

The rate of water absorption and thus the "wet tack" of the adhesive agent will be reduced.

By strengthening the cohesion the elastomeric matrix will have stronger elastic properties. When the hydrocolloids absorb water and swell, this will enhance an increase in the dimensions of the adhesive agent. Due to the elastic properties of the matrix, the tensions occurring in the adhesive agent cannot be relaxed by plastic deformation. Instead pleats may occur in the adhesive agent around the swelled area. In these pleats the adhesive agent will loose contact with the skin exposed to the body fluids, and a risk of leakage arises.

U.S. Pat. Nos. 4,192,785 and 4,551,490 describe incorporating into an adhesive composition a cohesive strengthening agent such as a natural or synthetic fibrous material, finely divided cellulose, cross-linked dextran, cross-linked carboxymethylcellulose or a starch-acrylonitrile graft copolymer. The cohesive strengthening agent is stated to control the rate of hydration of the composition thereby increasing the resistance against breakdown by body fluids.

U.S. Pat. No. 4,477,325 describes incorporation of a mixture of a copolymer resin of ethylene and vinyl acetate (EVA) into the adhesive composition. After mixing and moulding, the composition is subjected to ionising radiation to form a cross-linked polymer network of the EVA or comprising EVA and another cross-linked resin. The cross-linked matrix is said to provide a controlled swelling.

U.S. Pat. No. 4,496,357 describes the incorporation of fumed silica into adhesive compositions to control swelling.

EP No. 0 122 344 B1 describes incorporation of one or more natural or synthetic polymers capable of developing elastomeric properties when hydrated, such as gluten and long chain polymers of methyl vinyl ether/maleic acid, into the adhesive composition. The adhesive composition is stated to be resistant to erosion by moisture and body fluids.

EP Patent No. 0 340 945 B1 describes incorporation of some polycationic hydrocolloid particles into a hydrocolloid composition. The mixture of polycationic, polyanionic and neutral hydrocolloids is stated to provide increased integrity without a concomitant decrease in absorbing capacity.

In existing adhesive agents the surface of the adhesive is consisting of the self-adhesive elastomeric matrix while the hydrocolloids are located embedded beneath the surface in the elastomeric matrix. In order to be absorbed, the water thus needs to penetrate through the elastomeric matrix before reaching the water absorbing hydrocolloids. This retards the water-absorption and causes that the adhesive agent does not have an immediately adhesion to wet surfaces (wet tack).

Thus, there is still a need for an adhesive agent showing a very rapid water absorption and retention in order to improve the wet tack.

Skin problems associated with an ostomy are different from skin problems generally associated with adhesives for skin (dressings or plasters) as the adhesives of ostomy appliances are placed permanently at the same site during long periods of time (cronical irritation) whereas other adhesives for skin are normally only placed at the same site for a short period of time.

European Patent publication No. EP 0 017 401 A1 discloses articles of manufacture having adhesive properties useful for, for example, protective plasters or dressings or as rings, washers or the like in surgical appliances such as ostomy appliances comprising a plastics matrix comprising the product resulting from heating together one or more polyhydric alcohols and gelatine and/or naturally occurring high molecular weight polysaccharide gum and/or a resin which is a copolymer and a vinyl ether and an organic acid anhydride and/or its corresponding free acid. Polyvinylpyrrolidone resin may be added as a tack modifier.

European Patent publication No. EP 0 343 807 A2 discloses absorptive adhesive dressing with controlled hydration containing about 30–65% polyisobutylene, 10–30% polyvinylpyrrolidone, 2–20% modified starch, 2–20% pectin, 0.1–10% acrylic polymer and 0–1% fibre. The dressing disclosed in EP 0 343 807 A2 is a nonocclusive dressing providing a controlled water evaporation from the wound area.

European Patent publication No. EP 0 063 898 discloses a microporous tape comprising a porous backing layer and a microporous adhesive layer including a rubbery elastomer such as polyisobutylene, one or more water swellable hydrocolloids and other optional substances. A copolymer of polyvinylpyrrolidone and vinylacetate may be used as a tackifier.

European Patent publication No. EP 0 591 898 A1 discloses adhesive compositions and wound dressings comprising an adhesive composition comprising a blend of a hydrophobic unsaturated aliphatic homopolymer, a compatible tackifier and at least one hydrocolloid adsorbent which composition has been exposed to a dose of ionising radiation which chemically cross-links the unsaturated aliphatic homopolymer component.

It has surprisingly been found that the use of an adhesive comprising a conjugated diene polymer and a polyvinyl pyrrolidone polymer or a polyvinyl pyrrolidone vinylacetate copolymer improves the rate of absorption of water and improves the tack of an adhesive agent on wet skin and the cohesion of the adhesive agent and also improves the performance towards the action of aggressive exudates or excretions from a body without having to rely on the addition of other ingredients. Furthermore, it has surprisingly been found that the presence of an acrylic elastomer as a complementary binder is not necessary and that it is not necessary to have to rely on a chemical cross-linking and addition of a tackifier in order to obtain an adhesive composition showing satisfactory properties, physical cross-linking has been found to be sufficient.

BRIEF SUMMARY OF THE INVENTION

The invention relates to a pressure sensitive adhesive composition suitable for application to human or animal skin comprising a polyvinyl pyrrolidone polymer or a polyvinyl pyrrolidone vinylacetate copolymer. Furthermore, the invention relates to a method for preparing such adhesives and the use of such adhesive or the preparation of a wound dressing or a adhesive wafer for an ostomy appliance or the use of the adhesive agent for securing of and sealing around ostomy bandages, for securing wound dressings, for securing of devices for collecting urine, wound-drainage bandages, orthoses and prostheses and for protecting skin areas and parts of the body against pressure, impacts and friction.

DETAILED DESCRIPTION OF THE INVENTION

In a first aspect, the present invention relates to a pressure sensitive adhesive composition suitable for application to human or animal skin comprising a polyisobutylene polymer, a polyvinyl pyrrolidone polymer or a polyvinyl pyrrolidone vinylacetate copolymer, optionally one or more hydrocolloids and optionally a physically cross-linked elastomer selected from block-copolymers comprising styrene and one or more butadienes wherein the adhesive composition comprises 30–50% of a polyisobutylene polymer, 10–60% of a polyvinyl pyrrolidone polymer or 10–30% of a polyvinyl pyrrolidone vinylacetate copolymer, 0–50% of one or more hydrocolloids and 0–10% of a physically cross-linked elastomer selected from block-copolymers comprising styrene and one or more butadienes By introducing a polyvinyl pyrrolidone polymer or a polyvinyl pyrrolidone vinylacetate copolymer in a self-adhesive elastomeric matrix an improved adhesion in moist environment is achieved. This is ascribed to the fact that the polyvinyl pyrrolidone polymer is present also at the surface of the adhesive agent and thus is able to cause an immediately absorption of water. Due to the ability of the polyvinyl pyrrolidone polymer to absorb water, the amount of hydrocolloids in the form of traditional hydrocolloid particles may be reduced and it is even possible to avoid such hydrocolloids in the adhesive of the invention. The improved cohesion of the adhesive allows for a complete removal of the adhesive after the period of service without leaving residues on the skin when used for securing an ostomy appliance Polyvinylpyrrolidone (PVP) and vinylpyrrolidone/vinyl acetate copolymer (PVP/VA) provides a strong gel integrity. Compositions of the invention exhibit greater resistance to degradation by biological fluids than comparable adhesive compositions of the prior art. Furthermore, no residue of the adhesives of the invention remains on the skin upon removal of the adhesive.

PVP and PVP/VA are capable of absorbing water and proving a wet tack. Compositions of the invention therefore possess significantly enhanced adhesion on moist skin as compared to compositions of the state of the art.

Thus it has been found that it is possible to provide a pressure sensitive adhesive composition suitable for application to human or animal skin consisting essentially of a conjugated diene polymer, a polyvinyl pyrrolidone polymer or a polyvinyl pyrrolidone vinylacetate copolymer, optionally one or more hydrocolloids and optionally a physically cross-linked elastomer selected from block-copolymers comprising styrene and one or more butadienes and not having to rely upon chemical crosslinking in order to ensure a sufficient cohesion and also not having to rely upon addition of tackifiers in order to ensure a sufficient tack.

Furthermore, PVP and PVP/VA are hypo-allergenic and have for a long time been applied in the formulation of cosmetics and toiletries such as conditioning shampoos, setting lotions, skin-care products, etc. U.S. Pat. No. 5,320,838 describes that PVP together with poly-ethylene glycol forms a protectant for irritated skin. Similarly, JP 07265352 A discloses a patch agent for applying on a person having irritable skin in which PVP is also incorporated. Due to introducing of PVP and PVP/VA, compositions of the invention possess skin healing properties and provides comforts on the skin. Less pain is experienced upon removal.

In one embodiment of the invention, the adhesive composition consists only of a conjugated butadiene polymer, a polyvinyl pyrrolidone polymer or a polyvinyl pyrrolidone vinylacetate copolymer and one or more hydrocolloids. It has even been proved possible to prepare an adhesive composition according to the invention comprising only polyisobutylene and PVP having superior properties with respect to wet tack and rate of absorption of water.

Suitable hydrocolloids are naturally occurring hydrocolloids such as guar, locust bean gum (LBG), pectin, alginates, gelatine, xanthan or karaya, semisynthetic hydrocolloids such as cellulose derivatives (e.g., salts of carboxymethylcellulose, methylcellulose and hydroxypropylmethylcellulose), sodium starch glycolate and synthetic hydrocolloids such as polyvinylalcohol or polyethylene glycol.

The conjugated butadiene polymer used in the adhesive of the invention may be polybutadiene or polyisoprene and is preferably polybutadiene.

The physically cross-linked elastomer selected from block-copolymers comprising styrene and one or more butadienes may be a styrene-butadiene-styrene copolymer and is preferably styrene-isoprene-styrene copolymer.

The adhesive compositions of the invention may optionally comprise further components normally used in formulation of adhesive compositions such as pigments such as zinc oxide or titanium dioxide.

In a second aspect, the invention relates to a method for the preparation of a pressure sensitive adhesive composition of the invention wherein the conjugated diene polymer and the polyvinyl pyrrolidone polymer or a polyvinyl pyrrolidone vinylacetate copolymer are mixed during heating, whereafter optionally one or more hydrocolloids are admixed. When a physically cross-linked elastomer selected from block-copolymers comprising styrene and one or more butadienes is present, a premix of this elastomer with the conjugated diene polymer is formed before admixing with the polyvinyl pyrrolidone polymer or a polyvinyl pyrrolidone vinylacetate copolymer.

When carrying out the method of the invention, the mixing of the conjugated diene polymer and the polyvinyl pyrrolidone polymer or a polyvinyl pyrrolidone vinylacetate copolymer is carried out at temperature of from about 25° C. to about 225° C. More preferred, the mixing is carried out at a temperature of from 35° C. to about 180° C. When only mixing a conjugated diene polymer, a polyvinyl pyrrolidone polymer or a polyvinyl pyrrolidone vinylacetate copolymer and no physically cross-linked elastomer selected from block-copolymers comprising styrene and one or more butadienes, the temperature of mixing is suitably from 50° C. to about 100° C. When also admixing a physically cross-linked elastomer selected from block-copolymers comprising styrene and one or more butadienes, the temperature of mixing is suitably from 120° C. to about 180° C.

The method of the invention is advantageously carried out at a reduced pressure in order to avoid extensive degradation. The mixing is preferably carried out at a pressure of from 10 mbar to about 500 mbar and more preferably at from 20 to 100 mbar.

The resulting dough-like mass is then preferably removed from the mixer while hot and soft and formed into approximately 1 mm thick sheet stock material by compression moulding the adhesive mass at a temperature of from 50° C. to about 120° C., preferably approximately 90° C., and a pressure of from 50–150 bars, preferably about 100 bars, between two sheets of silicone release paper. The resultant flat plate may then be cut into the desired shapes.

In a further aspect, the invention relates to the use of a pressure sensitive adhesive composition of the invention for securing of and sealing around ostomy bandages, for securing wound dressings, for securing of devices for collecting urine, wound-drainage bandages, orthoses and prostheses or for protection skin areas and parts of the body against pressure, impacts and friction.

In a further aspect, the invention relates to ostomy appliances comprising a pressure sensitive adhesive composition of the invention.

Such appliances may be two-piece or one-piece appliances. In both types of appliances, a body side member is attached to the wearer's abdomen, and optionally a receiving member or bag is attached to the body side ostomy member for receiving secretions from the ostomy in case of a two-piece appliance. Such appliances are used in connection with surgery for a number of diseases in the gastro-intestinal tract where the patient is left with an abdominal stoma such as a colostomy, an ileostomy or an urostomy to collect the bodily material emerging from such opening.

An ostomy appliance of the invention may have any form and be made from any material known per se in connection with ostomy appliances. A body side member of such an appliance preferably comprises a substantially water-impervious layer or film and the adhesive according to the invention and the adhesive surface is optionally covered in part or fully by one or more release liners or cover films to be removed before or during application.

In yet a further aspect, the invention relates to a wound dressing said dressing comprising a substantially water-impervious layer or film and a pressure sensitive adhesive according to the invention which dressing is optionally covered in part or fully by one or more release liners or cover films to be removed before or during application.

The water impervious layer or film may be of any suitable material known per se for use in the preparation of wound dressings e.g. a foam, or a polyurethane, polyethylene, polyester or polyamide film. In accordance with the invention it has surprisingly been found that when using a thinner backing layer or film than is normally used when preparing medical dressings, an improved stretcheability and adaptability is obtained at the same time as the modulus is reduced. These properties are obtained using the same load of adhesive as is conventionally used, and thus, the conventional properties of the adhesive are retained as opposed to the case in which the load of adhesive was lowered giving a risk of insufficient tack and adhesive properties.

The water impervious layer or film is preferably a low-friction flexible polymer film reducing the risk of unwanted stress in the area of a skin crack impeding the healing of a crack on a very exposed site.

A dressing or ostomy appliance of the invention preferably has bevelled edges in order to reduce the risk of "rolling-up" the edge of the dressing reducing the wear-time. A bevelling may be carried out discontinuously or continuously in a manner known per se, e.g., as disclosed in EP Patent No. 0 264 299 or in U.S. Pat. No. 5,133,821.

A protective cover or release liner may for instance be siliconized paper. It does not need to have the same contour as the dressing, e.g., a number of dressings may be attached to a larger sheet of protective cover. The protective cover is not present during the use of the dressing of the invention and is therefore not an essential part of the invention.

Furthermore an ostomy appliance or wound dressing of the invention may comprise a "non touch" grip known per se for applying the dressing to the skin without touching the adhesive layer. Such a non-touch grip is not present after application of the dressing.

It is advantageous to provide an ostomy appliance or wound dressing of the invention with components for treatment or prophylaxis of formation of wounds and/or skin abnormalities, e.g., with emollients or an active constituent, e.g., retinoids for treating or preventing formation of psoriasis, eczema, callous skin, corns, insect bites, acne or blisters. The dressing of the invention may also contain medicaments such as bacteriostatic or bactericide compounds, e.g., iodine, iodopovidone complexes, chloramine, chlorohexidine, silver salts, zinc or salts thereof, tissue-healing enhancing agents, e.g., RGD tripeptides and the like, enzymes for cleansing of wounds, e.g., pepsin, trypsin and the like, pain relieving agents, or agents having a cooling effect which is also considered an aspect of the invention.

The invention is explained more in detail with reference to the below working examples disclosing embodiments of the invention which are to be considered illustrative only of principles of the invention. As all suitable modifications and equivalents may be resorted to, the examples are not to be considered as limiting the scope of the invention set forth in the appended claims.

Materials and Methods

PIB: Polyisobutylene available under the trademark Vistanex from Exxon Chemical Co. as grade LM-MH.

PVP K-90: Polyvinylpyrrolidone available from ISP Inc. having a molecular weight of 630,000.

PVP/VA S-630: Vinylpyrrolidone/vinyl acetate copolymer available from ISP Inc. with a mole ratio of VP/VA 60/40.

Kraton D1107: Styrene-isoprene-styrene copolymer having a molecular weight of 212,000–260,000 (GPC) and a content of diblock of 15–25%.

Gelatine: Gelatine P.S.98.240.233 available from ED. Geistlich Sohne AG.

Pectin: Pectin LM 12CG Z or Pectin USP/100 from Copenhagen Pectin A/S.

CMC: Sodium carboxymethylcellulose available from Akzo under the tradename Akucell® AF2881 or from Hercules Corp. under the tradename Blanose® 9H4XF.

A Z mixer Type LKB 025 from Herman-Linden was used.

Experimental Part

EXAMPLE 1

Preparation of an adhesive material according to the invention.

An adhesive having the following composition was prepared:

| Ingredient | Percent by weight |
| --- | --- |
| PIB | 40 |
| PVP/VA S-630 | 15 |
| Gelatine | 15 |
| Pectin | 20 |
| CMC | 10 |

80 grams of PIB and 30 grams of PVP/VA S-630 were mixed in a Z mixer for 10 minutes at 80° C. and mixing was then continued under a vacuum of 50 mbar for further 10 minutes. Then, the vacuum was released, and 30 grams of Gelatine, 40 grams of Pectin and 20 grams of CMC were added and mixed for 15 minutes and the mixing was continued under a vacuum of 50 mbar until a homogeneous dough-like mass was formed.

This dough-like mass was then removed from the mixer while hot and soft and formed into approximately 1 mm thick sheet stock material by compression moulding the adhesive mass at approximately 90° C. and 100 Bars between two sheets of silicone release paper. The resultant flat plate was then cut into the desired shapes.

EXAMPLES 2–9

Following the procedure of Example 1 the adhesive compositions stated in the below Tables were prepared:

| Ingredient | Example 2 | Example 3 | Example 4 | Example 5 |
| --- | --- | --- | --- | --- |
| PIB | 40 | 40 | 40 | 45 |
| PVP/VA S-630 | 15 | 30 | 20 | 15 |
| Gelatine | 15 |  | 10 | 10 |
| Pectin pomosin | 15 |  | 10 | 20 |
| CMC | 15 | 30 | 20 | 10 |

| Ingredient | Example 6 | Example 7 | Example 8 | Example 9 |
| --- | --- | --- | --- | --- |
| PIB | 40 | 42.5 | 37.5 | 45 |
| PVP/VA S-630 | 20 | 12.5 | 17.5 | 15 |
| Gelatine | 10 | 15 | 15 | 10 |
| Pectin pomosin | 10 | 15 | 15 | 10 |
| CMC | 20 | 15 | 15 | 20 |

EXAMPLES 10–16

Following the procedure of Example 1 with the exception that the temperature was increased to 90° C., the adhesive compositions stated in the below Tables were prepared:

| Ingredient | Example 10 | Example 11 | Example 12 | Example 13 |
| --- | --- | --- | --- | --- |
| PIB | 40 | 40 | 40 | 40 |
| PVP K-90 | 10 | 30 | 60 | 10 |
| Gelatine | 20 |  |  | 15 |

-continued

| Pectin pomosin | 15 | | 20 |
| CMC | 15 | 30 | 15 |

| Ingredient | Example 14 | Example 15 | Example 16 |
| --- | --- | --- | --- |
| PIB | 40 | 40 | 40 |
| PVP K-90 | 20 | 30 | 15 |
| Gelatine | 10 | | 15 |
| Pectin pomosin | 10 | 10 | 15 |
| CMC | 20 | 20 | 15 |

EXAMPLE 17

Preparation of an adhesive material according to the invention.

A premix powder was prepared by blending 30 grams of PVP/VA S-630, 30 grams of Gelatine 30 grams of Pectin and 30 grams of CMC.

The PIB (100 grams) was added in a Z mixer at 150° C. and softened for 5 minutes. To this was added 100 grams of Kraton® D1107 and the mixing was continued under 150° C. and 50 mbar until the blend was homogeneous. The mass was cooled to 80° C., and 168 grams of the mass was removed from the mixer. To this remaining mass was added the powdered premix. The mixing was continued under 80° C. and 50 mbar until a homogeneous dough-like mass was formed.

This dough-like mass was then removed from the mixer while hot and soft and formed into approximately 1 mm thick sheet stock material by compression moulding the adhesive mass at approximately 90° C. and 100 bar between two sheets of silicone release paper. The resultant flat plate was then cut into the desired shapes.

EXAMPLES 18–20

Following the procedure of Example 17 the adhesive compositions stated in the below Table (also showing the composition of Example 17) were prepared:

| Ingredient | Example 17 | Example 18 | Example 19 | Example 20 |
| --- | --- | --- | --- | --- |
| PIB | 32 | 32 | 32 | 35 |
| PVP K-90 | | | 10 | 12 |
| PVP/VA S-630 | 15 | 20 | | |
| Kraton D1107 | 8 | 8 | 8 | 8 |
| Gelatine | 15 | 10 | 17.5 | 10 |
| Pectin pomosin | 15 | 15 | 10 | 15 |
| CMC | 15 | 15 | 22.5 | 20 |

EXAMPLE 21

Testing of adhesive compositions according to the invention.

Body side members having an adhesive wafer comprising an adhesive according to the invention having the composition stated in Examples 1 and 16 were prepared.

The body side members were tested on 25 healthy volunteers each and compared with a commercial Coloplast Assura one piece appliance with respect to flexibility, residue on the skin after removal, pain during removal, and resistance against erosion.

The results showed that both adhesives comprising polyvinyl pyrrolidone polymer and a polyvinyl pyrrolidone vinylacetate copolymer, respectively, provided significant improvement with regards to the flexibility, residue on skin after removal, pain during removal, and resistance against erosion.

What is claimed is:

1. A pressure sensitive adhesive composition suitable for application to human or animal skin and comprising a) from 30–50% of a polyisobutylene polymer, from 10–60% of a polyvinyl pyrrolidone polymer or from 10–30% of a polyvinyl pyrrolidone vinylacetate copolymer, b) a pigment selected from the group consisting of zinc oxide and titanium dioxide, c) from 0–50% of one or more hydrocolloids and d) from 0–10% of a physically cross-linked elastomer selected from the group consisting of a block-copolymer comprising styrene and one or more butadienes.

2. A pressure sensitive adhesive composition as claimed in claim 1, wherein the physically cross-linked elastomer is a styrene-isoprene-styrene copolymer.

3. A wound dressing comprising a pressure sensitive adhesive according to claim 1 and a substantially water-impervious layer or film which dressing is optionally covered in part or fully by one or more release liners or cover films to be removed before or during application.

4. An ostomy appliance comprising a pressure sensitive adhesive composition according to claim 1, and optionally comprising a substantially water-impervious layer or film and the adhesive surface of which is optionally covered in part or fully by one or more release liners or cover films to be removed before or during application.

5. A method of using a pressure sensitive adhesive composition according to claim 1 for securing of and sealing around ostomy bandages, for securing wound dressings, for securing of devices for collecting urine, wound-drainage bandages, orthoses and prostheses or for protection of skin areas and parts of the body against pressure, impacts and friction, comprising applying the composition to human or animal skin.

6. A pressure sensitive adhesive composition as claimed in claim 1 comprising 32 to 45% of polyisobutylene polymer, 10 to 60% of polyvinyl pyrrolidone polymer or 15 to 30% of polyvinyl pyrrolidone vinylacetate copolymer, 0 to 45% of hydrocolloid and 0 to 8% of a physically cross-linked elastomer.

7. A pressure sensitive adhesive composition suitable for application to human or animal skin and which consists essentially of (a) polyisobutylene polymer, and a member selected from the group consisting of (b) a polyvinyl pyrrolidone polymer and (c) a polyvinyl pyrrolidone vinylacetate copolymer; said composition comprising from 30 to 50% of (a), the amount of (b), when present, being from 10 to 60%, and the amount of (c), when present, being from 10 to 30%.

8. A pressure sensitive adhesive composition of claim 7 which further comprises a member selected from the group consisting of (d) a hydrocolloid and (e) a physically cross-linked elastomer which is a block-copolymer of styrene and a butadiene; said composition comprising from 0 to 50% of (d) and from 0 to 10% of (e).

9. A method which comprises applying a pressure sensitive adhesive composition of claim 7 to human or animal skin to secure thereto or seal around an ostomy bandage, to secure thereto a wound dressing, to secure thereto a device for collecting urine, a wound-drainage bandage, a device for orthosis, a prosthesis or a device for protecting a skin area or body part against pressure, impact or friction.

10. A wound dressing comprising a pressure sensitive adhesive according to claim 7 and a substantially water-impervious layer or film, which dressing is optionally covered in part or fully by one or more release liners or cover films to be removed before or during application.

11. An ostomy appliance comprising a pressure sensitive adhesive composition according to claim 7, and optionally comprising a substantially water-impervious layer or film and the adhesive surface of which is optionally covered in part or fully by one or more removable release liners or cover films.

12. A pressure sensitive adhesive composition as claimed in claim 7 comprising from 32 to 45% of polyisobutylene polymer, from 10 to 60% of polyvinyl pyrrolidone polymer, from 15 to 30% of polyvinyl pyrrolidone vinylacetate copolymer, from 0 to 45% of hydrocolloid and from 0 to 8% of a physically cross-linked elastomer.

13. A pressure sensitive adhesive composition as claimed in claim 8, wherein the physically cross-linked elastomer is a styrene-isoprene-styrene copolymer.

* * * * *